United States Patent [19]

Carroll et al.

[11] Patent Number: 5,610,706
[45] Date of Patent: *Mar. 11, 1997

[54] ANALYSIS SYSTEM

[75] Inventors: Charles E. Carroll, Kingston, N.H.; Garry C. Kunselman, Stow, Mass.; Arthur E. Tobey, Salem, N.H.

[73] Assignee: Thermo Jarrell Ash Corporation, Franklin, Mass.

[*] Notice: The term of this patent shall not extend beyond the expiration date of Pat. No. 5,521,698.

[21] Appl. No.: 191,395

[22] Filed: Feb. 2, 1994

[51] Int. Cl.$^6$ .................... G01N 21/67; G01N 21/35; G01N 33/26

[52] U.S. Cl. ................ 356/70; 356/72; 356/73; 356/313

[58] Field of Search ............... 356/70–73, 313, 356/440

[56] References Cited

U.S. PATENT DOCUMENTS

| | | | |
|---|---|---|---|
| 3,526,127 | 9/1970 | Sarkis | 356/70 X |
| 3,645,628 | 2/1972 | Bojic et al. | 356/313 |
| 4,367,043 | 1/1983 | Sweet et al. | 356/440 X |
| 4,469,441 | 9/1984 | Bernier et al. | 356/316 |
| 4,618,769 | 10/1986 | Johnson et al. | 356/440 |
| 5,064,283 | 11/1991 | Tober | 356/73 |
| 5,141,314 | 8/1992 | Belmore et al. | 356/313 |
| 5,207,905 | 5/1993 | O'Brien et al. | |
| 5,278,629 | 1/1994 | Schlager et al. | 356/313 |

FOREIGN PATENT DOCUMENTS 63-266342  11/1988  Japan ........................ 356/70

OTHER PUBLICATIONS

Detect Auto Labs, Inc., "Blood Test for Your Engine", 1988.
Garry, *Nicolet Instrument Corporation*, "Applied Interpretation of FT–IR Oil Analysis Results for Improving Predictive Maintenace Programs", 1991.

*Primary Examiner*—Vincent P. McGraw
*Attorney, Agent, or Firm*—Fish & Richardson P.C.

[57] ABSTRACT

An analytical system for analyzing a liquid sample includes structure defining an analysis region with an inlet and an outlet, a polychromator system disposed in sensing relation to the analysis region, structure defining a sample inlet port, and structure connecting the sample inlet port to the inlet of the analysis region. The analysis region includes sample excitation apparatus with a pair of spaced metal electrodes, one of the electrodes having an upper surface in spaced juxtaposition to the other electrode and passage structure connected to the inlet of the analysis region. The one metal electrode is disposed with the passage structure extending to an outlet port in the upper surface, and structure in the upper surface defines a plurality of channels extending away from the outlet port of the passage structure for discharge of excess quantities of a liquid sample to be analyzed flowed through the passage structure. Control structure flows a sample to be analyzed from the sample inlet port through the analysis region, and output structure coupled to the analysis region provides output data as a function of the output of the polychromator system.

33 Claims, 3 Drawing Sheets

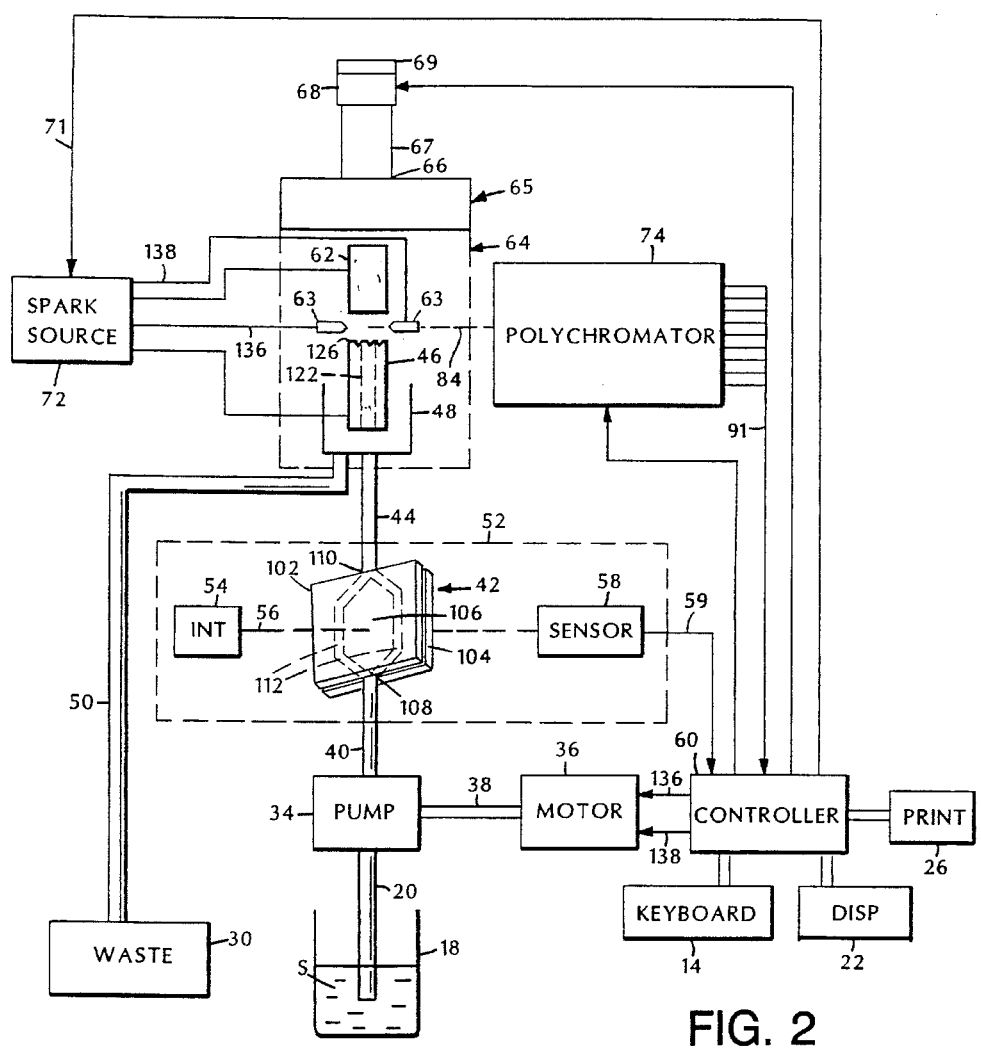

ANALYSIS SYSTEM

This invention relates to analysis systems, and more particularly to apparatus and processes for analyzing liquid samples such as engine oils and the like, and to spectrometer methods and apparatus.

BACKGROUND OF THE INVENTION

Analysis of constituents of engine oil provides information on current conditions of the engine and may identify problems which may require costly repair if not corrected. Analytical services of this type have been provided through use of a kit type service in which a sample of the engine oil is mailed to an analysis laboratory and a report is furnished after the laboratory conducts an analysis using conventional analysis equipment such as a polychromator with rotatable carbon electrodes. Such technology involves a delay of several days. Improved maintenance of engines, vehicles and other equipment could be obtained by providing analytical equipment in the garage or other maintenance facility for use by a technician operating in a shop environment.

SUMMARY OF THE INVENTION

In accordance with one aspect of the invention, there is provided an analysis system with a sample input, a first sample analysis region with two parallel plates through which a beam of radiation is passed for FTIR analysis and a second sample analysis region that includes a pair of spaced electrodes for exciting the sample material to spectroemissive levels and a spectroanalytical system coupled to the electrodes for responding to radiation from the electrode gap.

In accordance with another aspect of the invention, there is provided an analytical system for analyzing a liquid sample that includes housing structure, structure in the housing structure defining a first analysis region having an inlet and an outlet, a FTIR analysis system disposed in sensing relation to the first analysis region, structure in the housing structure defining a second analysis region having an inlet and an outlet, a polychromator system disposed in sensing relation to the second analysis region, structure defining a sample inlet port, structure connecting the sample inlet port to the inlets of the first and second analysis regions, control structure in the housing structure for flowing a sample to be analyzed from the sample inlet port through the first and second analysis regions, and output structure coupled to the first and second analysis regions for providing output data as a function of the outputs of the FTIR system and the polychromator system as a function of the liquid sample flowed through the first and second analysis regions.

In a particular embodiment, the FTIR analysis system includes a flow through cell with a pair of spaced plate members, the first analysis region is disposed between the plate members, interferometer structure that generates a beam of radiation for passage through the plate members and the first analysis region, and sensor structure that senses the beam of radiation passed through the plate members and the first analysis region for generating FTIR analysis information as function of the liquid sample disposed in the first analysis region. The polychromator system includes entrance slit structure, exit slit structure composed of a plurality of exit slit regions, and radiation dispersing structure for dispersing radiation passing through the entrance slit structure into a spectrum for application to the exit slit regions. The second analysis region includes sample excitation apparatus with main and trigger electrodes disposed in an enclosed chamber with an outlet port across which filter structure is disposed, and fan structure for flowing gas from the chamber through the filter structure for exhaust outside the housing structure. The main electrodes are a pair of spaced metal electrodes (preferably of at least 99% purity), one of the electrodes having an upper surface in spaced juxtaposition to the other electrode and a through passage connected to the inlet of the second analysis region, the one metal electrode being disposed with the through passage extending to an outlet port in the upper surface, and structure in the upper surface defining a plurality of channels extending away from the outlet port of the through passage for discharge of excess quantities of a liquid sample to be analyzed flowed through the through passage. The control structure for flowing a sample includes a pump that has forward and reverse modes of operation, the first and second analysis regions are connected in series, and the control structure flows a sample to be analyzed at a first flow rate into the first analysis region with the pump being stopped during an FTIR analysis cycle, and the pump being operated in a reverse flow mode (preferably less than one-half the first flow rate) during a first part of a polychromator analysis cycle to remove excess sample material from the second analysis region and then in a relatively low forward flow rate mode during a second part of the polychromator analysis cycle. The housing structure is mounted on wheels so that the analysis system is relatively mobile, and the polychromater system is mounted on shock absorbing structure.

In accordance with another aspect, there is provided a process for analyzing liquid sample material such as a lubricating oil comprising the steps of providing a first analysis region with an FTIR analysis system disposed in sensing relation to the first analysis region, providing structure defining a second analysis region with a polychromator system disposed in sensing relation to the second analysis region, flowing a liquid sample to be analyzed into the first analysis region, stopping the liquid sample flow while said liquid sample is in the first analysis region and subjecting that liquid sample in the first analysis region to an FTIR analysis sequence, flowing the liquid sample into the second analysis region, reversing the flow direction to remove excess sample from the second analysis region, resuming flow in the forward direction at a low flow rate and concurrently subjecting the liquid sample in the second analysis region to an electric discharge to excite the liquid sample to spectroemissive levels for sensing by the polychromator system.

In accordance with another aspect, there is provided an analytical system that includes structure defining an analysis region, a spectrometer system disposed in sensing relation to the analysis region, the analysis region including sample excitation apparatus with a pair of spaced main electrodes, and a pair of trigger electrodes disposed in spaced relation to the main electrodes in the analysis region such that the breakdown of the gap between the trigger electrodes is adapted to generate ultraviolet radiation to preionize the gap between the main electrodes, and output structure coupled to the analysis region for providing output data as a function of the output of the spectrometer system as a function of sample material in the analysis region.

In accordance with still another aspect, there is provided an analytical system for analyzing a liquid sample comprising structure defining an analysis region with an inlet and an outlet, a spectrometer system disposed in sensing relation to the analysis region, structure defining a sample inlet port, structure connecting the sample inlet port to the inlet of the analysis region, the analysis region includes sample excitation apparatus with a pair of spaced metal electrodes, one of the electrodes having an upper surface in spaced juxtaposition to the other electrode and passage structure connected to the inlet of the analysis region. The one metal electrode is disposed with the passage structure extending to an outlet port in the upper surface, and structure in the upper surface defining a plurality of channels extending away from the outlet port of the passage structure for discharge of excess quantities of a liquid sample to be analyzed flowed through the passage structure. Control structure flows a sample to be analyzed from the sample inlet port through the analysis region, and output structure coupled to the analysis region provides output data as a function of the output of the spectrometer system as a function of the liquid sample flowed through the analysis region.

Preferably, the control structure for flowing a sample includes a pump that has forward and reverse modes of operation, and the control structure operates the pump in a reverse flow mode (preferably less than one-half the first flow rate) during a first part of a spectrometer analysis cycle to remove excess sample material from the analysis region and then in a relatively low forward flow rate mode during a second part of the spectrometer analysis cycle. The sample excitation apparatus (including both main and trigger electrodes) is preferably disposed in an enclosed chamber that has an outlet port across which filter structure is disposed, and fan structure flows gas from the chamber through the filter structure for exhaust.

In a particular embodiment, the spectrometer system is a polychromator that includes entrance slit structure, exit slit structure composed of a plurality of exit slit regions, and radiation dispersing structure for dispersing radiation passing through the entrance slit structure into a spectrum for application to the exit slit regions; the housing structure is mounted on wheel structure so that the analysis system is relatively mobile; and the housing structure includes shock absorbing structure, on which the polychromator system is mounted.

BRIEF DESCRIPTION OF THE DRAWING

Other features and advantages of the invention will be seen as the following description of a particular embodiment progresses, in conjunction with the drawings, in which:

FIG. 2 is a block diagram of the system shown in FIG. 1 including diagrammatic showings of the sample flow path and the analysis regions;

FIGS. 6–8 are side, top and bottom views of the lower arc stand electrode employed in the spectroscopy component of the system shown in FIG. 1; and FIG. 9 is a timing diagram indicating a sequence of operations with the system of FIG. 1.

DESCRIPTION OF PARTICULAR EMBODIMENT

Figure 1:
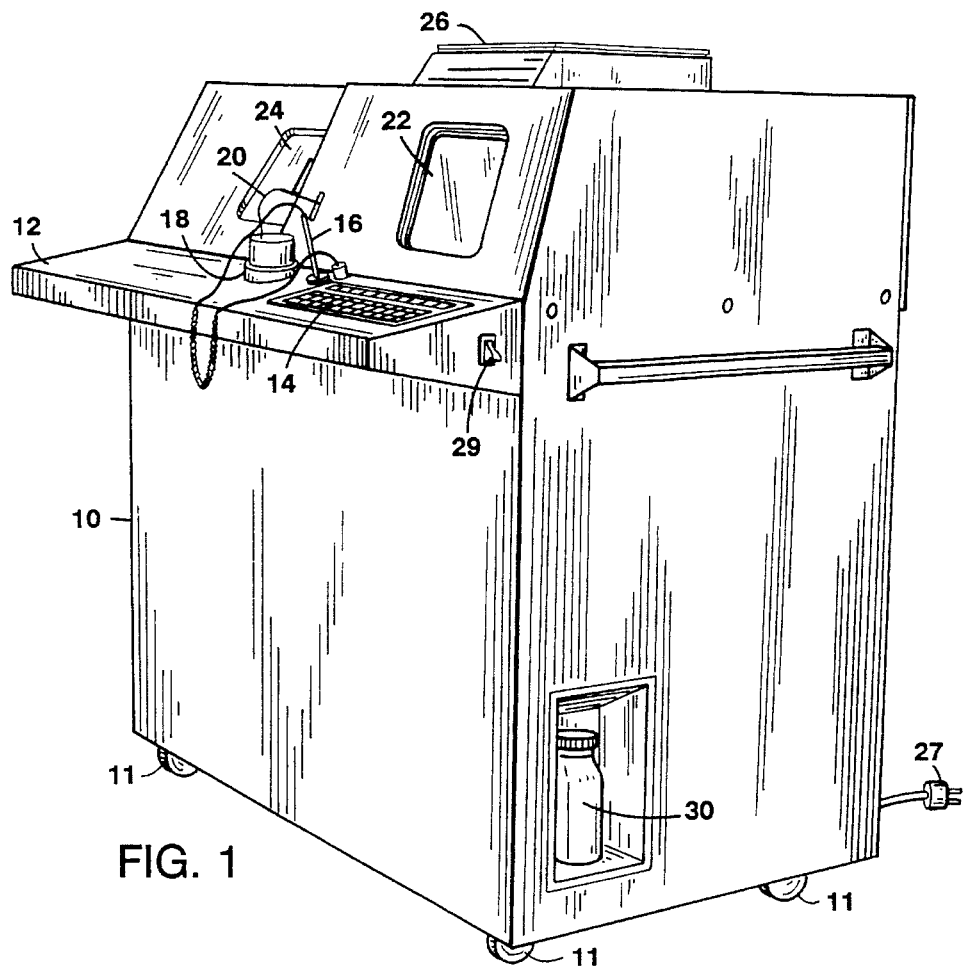
FIG. 1 is a perspective view of an analysis system in accordance with the invention.

The system shown in FIG. 1 includes mobile housing 10 mounted on wheels 11 with shelf 12 on which is mounted control keyboard 14, light pen type bar code reader 16, and oil sample receiver 18. Coupled to sample receiver 18 is one millimeter inner diameter stainless steel sipper nozzle 20. Mounted in the console above surface 12 are display 22 and arc stand chamber access door 24. A second output device in the form of printer 26 is disposed on top of the housing 10, 115 volt line cord 27 supplies electrical power to the system under control of switch 29, and waste container 30 is disposed in the end wall. Controller 60 is mounted in housing 10 behind display 22.

With reference to FIGS. 2–5, coupled to input tube 20 is variable displacement piston pump 34 driven by stepper motor 36 through timing belt 38. The output of pump 34 is coupled over line 40 to inlet 108 of FTIR flow through cell 42 and from outlet 110 of cell 42 over line 44 to through passage 122 of silver spark source electrode 46. Oil overflows from the top surface 126 of electrode 46 and flows into well 48 for transfer over line 50 to waste bottle 30.

FTIR system 52, which may be a Nicolet Impact 400 system, includes interferometer 54 that directs radiation beam 56 through flow cell 42 to sensor 58 that applies output signals over line 59 to controller 60.

Figure 4:
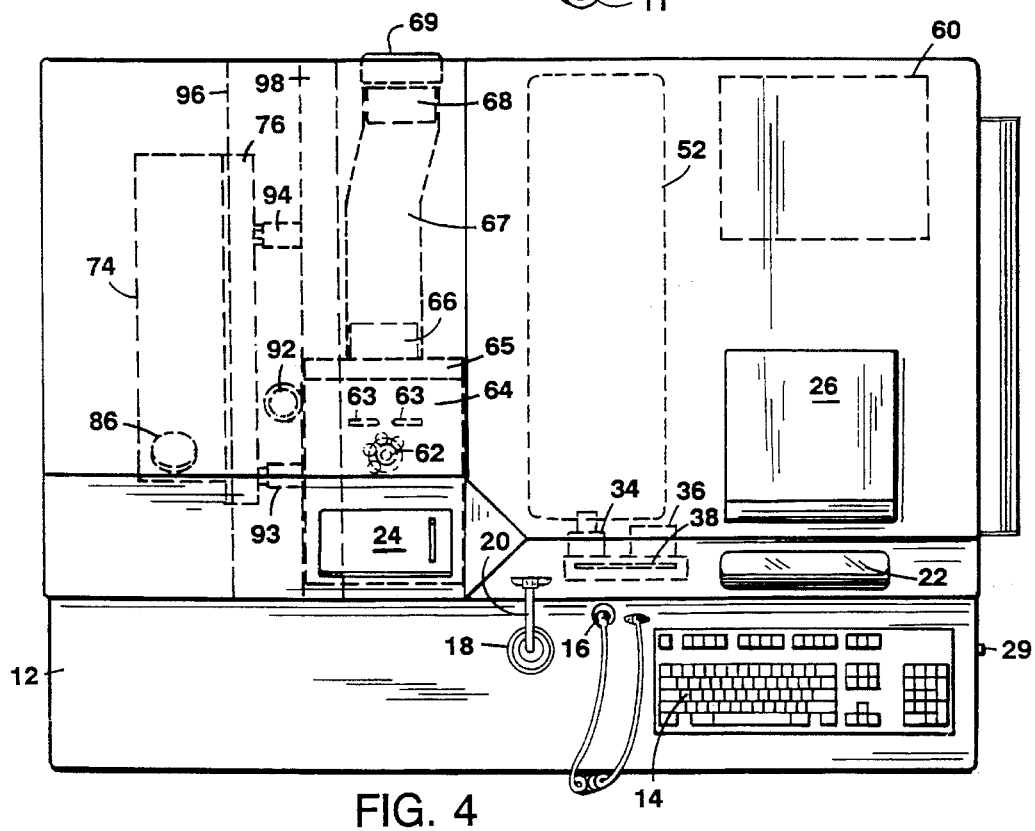
FIG. 4 is a top view of the system shown in FIG. 1.
Figure 3:
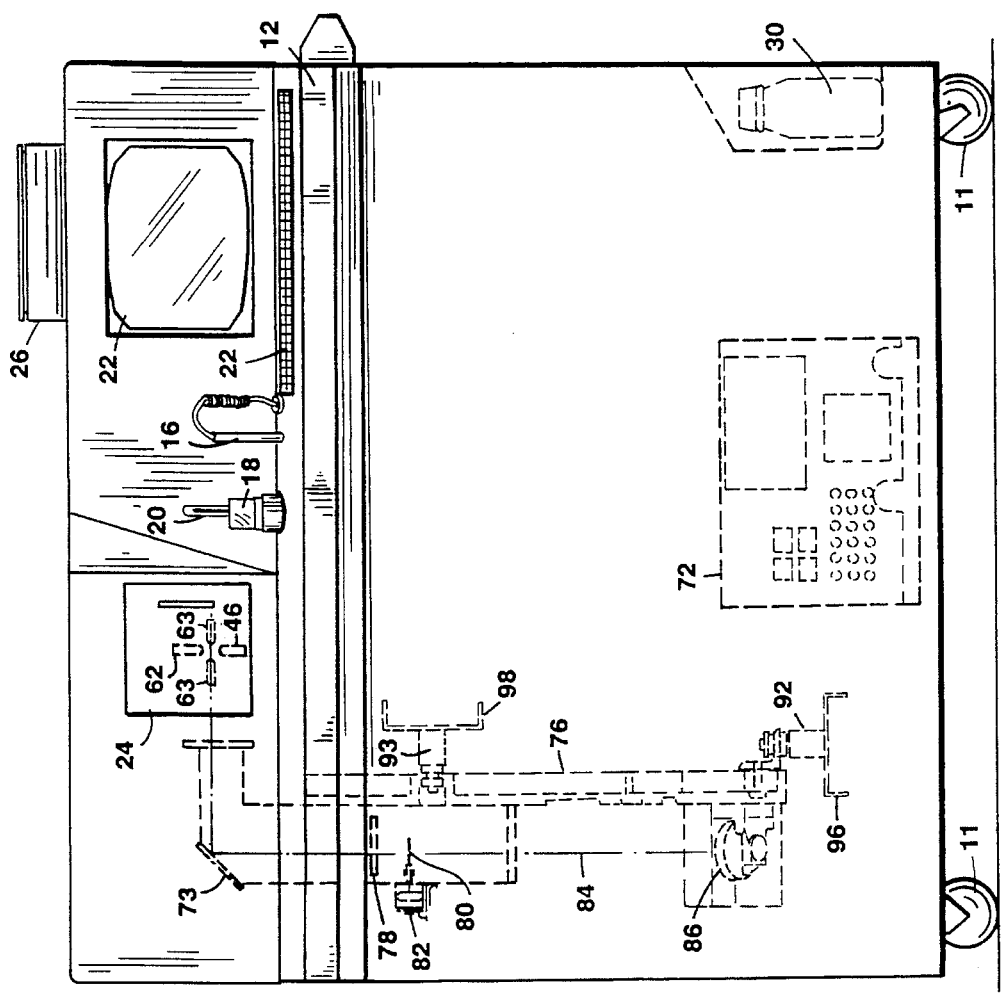
FIG. 3 is a front view of the system shown in FIG. 1.
Figure 5:
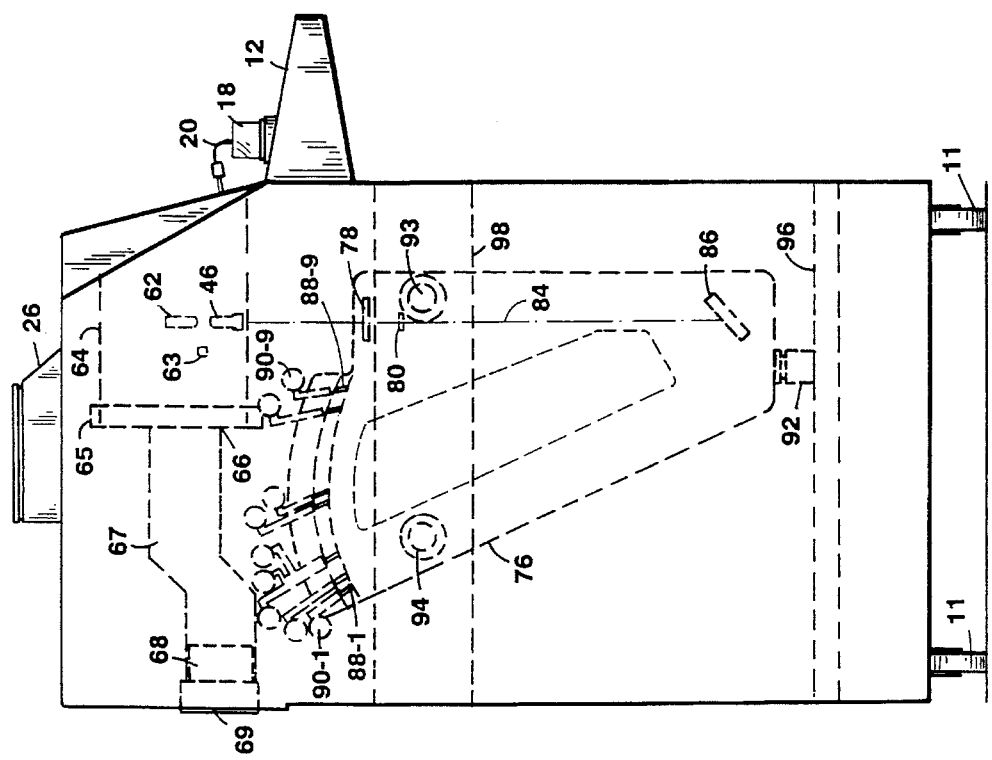
FIG. 5 is a side view of the analysis shown in FIG. 1.

The spark source also includes upper main electrode 62 and trigger electrodes 63 that are housed in chamber 64 that has access door 24 in its front wall. As shown in FIGS. 2, 4 and 5, chamber 64 has an activated charcoal and particulate filter 65 disposed across exhaust port 66 in its rear wall and tube 67 couples port 66 to exhaust fan 68 and exhaust port 69 in the rear wall of housing 10.

Mounted in the lower part of housing 10 is spark source unit 72 of the type shown in Belmore U.S. Pat. No. 5,141, 314 (the disclosure of which is expressly incorporated herein) and that receives control signals over lines 71 from controller 60 and energizes trigger electrodes 63 and main electrodes 46, 62 to generate sparks across the electrode gap to excite the oil sample to be analyzed to spectroemissive levels.

Optically coupled to the gap between electrodes 46 and 62 via mirror 73 (FIG. 3) is three quarter meter, nine channel polychromator unit 74 that includes frame 76 on which are mounted radiation dispersing grating 86, ten micrometer wide entrance slit structure 78, and spectrum shifter 80 driven by stepper motor 82 that is disposed in beam path 84 that is incident on grating 86. Radiation dispersed by gramting 86 passes through nine seventy-five micrometer wide exit slit structures 88 that are also mounted on frame 76 and is sensed by nine corresponding photomultiplier tubes 90. Spectrometer unit 74 is mounted on Lord shock mountings 92–94 that are in turn mounted on housing frame members 96, 98.

The photomultiplier tubes 90 are disposed to sense elementary aluminum, copper, iron, potassium, phosphorous, zinc, silicon, chromium, and tin and apply signals over lines 91 to controller 60. The FTIR sensor system 52 provides signals over line 59 for analyses of the oil sample for constituents such as glycol, water, fuel (gasoline or diesel) and soot.

The FTIR flow through cell 42 includes two potassium bromide plates 102, 104 spaced about 0.1 millimeter apart to provide a flow through sensing region 106 in which the oil sample to be analyzed is disposed and through which beam 56 is passed with an inlet 108 at the bottom and an outlet 110 at the top. Grooves 112 in the surface of plate 104 provides bypass channels that bypass sensing region 106 for release of bubbles and permit a faster oil flow pumping rate.

Shown in FIGS. 6–8 are top, side and bottom views of 99.999% pure silver spark electrode 46. Upper electrode 62 is of the same purity silver. Electrode 46 has a diameter of about 0.6 centimeter, and a length of about 1.5 centimeter. The lower portion of electrode 46 has threaded section 120 of about 0.6 centimeter length and through passage 122 of about one millimeter diameter. Formed in upper surface 126 is a waffle-like array 128 of V-shaped grooves 130 spaced about 0.12 millimeter on center in rectangular pattern and crests 132, each groove 130 being about 0.1 millimeter deep and with side walls at a 30° angle.

Trigger electrodes 63 are 1.5 millimeter diameter thoriated tungsten pointed rods that are disposed in spaced alignment and about two centimeters to the rear of electrodes 46, 62 and perpendicular to main electrodes 46, 62. The source 72 breaks down the trigger gap and the resulting ultraviolet radiation preionizes the main gap and assists in the breakdown of that gap with a spark striking to the electrode crests 132 and exciting the oil in grooves 130 to spectroemissive levels. The triggering signals on lines 136, 138 are generated at a 120 hertz repetition rate and each main spark is of about 800 microseconds duration and about twenty amperes magnitude.

In system use, oil from the sample S to be analyzed in sample container 18 is sucked through probe 20 by pump 34 for flow through FTIR sensing region 106 between plates 102, 104 of FTIR cell 42 and then through passage 122 of lower silver electrode 46 for flow into the electrode gap and overflow along the grooves 130 in upper surface 126 and then through collection well 48 and over line 50 to waste bottle 30.

With reference to FIG. 9, system controller 60 at the start 134 of an analysis cycle operates pump 34 by a signal over line 136 in the forward direction to provide a flow rate of about one milliliter per minute during flush interval 140 for a duration of about sixty seconds; an FTIR sample integral 142 (of about thirty seconds duration) during which the pump 34 is stopped for FTIR analysis and radiation beam 56 from interferometer 54 is passed through sensing region 106 of sample cell 42 for detection by sensor 58; a positive flow interval 144 of about fifteen seconds interval at one milliliter per minute flow rate to flow the oil into the grooves 130 of silver electrode 46; a reverse flow interval 146 (in response to a controller signal on line 138) of about fifteen seconds duration to suck excess oil from above the grooves 130 and expose crests 132 and then an analysis interval 148 (of about thirty seconds duration—about fifteen seconds preburn and about fifteen seconds integration) during which oil is flowed at a flow rate of about 0.1 milliliter per minute through passage 122 and grooves 130 while the electrodes 46, 62 are energized by spark source unit 72 to excite the oil sample to spectroemissive levels and to produce radiation beam 84 for sensing by polychromator unit 74.

The oil samples typically are of used engine and transmission lubricating oils and the like, engine oils being filtered to forty microns so that maximum particle sizes are 200 micrometers diameter. The time between end of measurement of a previous sample and beginning of measurement of the next sample is less than 45 seconds and sample cross contamination is less than five percent of the previous sample intensity. The resolution of the system polychromator 74 is better than 0.05 micrometer for all element wavelengths sensed by the photomultiplier tubes 90. The sample consumption rate for the emission and infrared measurements is less than ten milliliters and data collection is achieved in less than two minutes with a total sequence time from start of measurement to the end of printout of less than three minutes. The system typically will be used in a garage or other maintenance facility by a technician operating in a shop environment.

While a particular embodiment of the invention has been shown and described, various modifications will be apparent to those skilled in the art, and therefore, it is not intended that the invention be limited to the disclosed embodiment, or to details thereof, and departures may be made therefrom within the spirit and scope of the invention.

What is claimed is:

1. An analytical system for analyzing a liquid sample comprising housing structure, structure in said housing structure defining a first analysis region having an inlet and an outlet, a FTIR analysis system disposed in sensing relation to said first analysis region, structure in said housing structure defining a second analysis region having an inlet and an outlet, a polychromator system disposed in sensing relation to said second analysis region, sample excitation apparatus disposed in said second analysis region, said sample excitation apparatus including a pair of spaced metal electrodes, one of said electrodes having an upper surface in spaced juxtaposition to the other electrode and a through passage connected to said inlet of said second analysis region, said one metal electrode being disposed with said through passage extending to an outlet port in said upper surface, and structure in said upper surface defining a plurality of channels extending away from said outlet port of said through passage for discharge of excess quantities of a liquid sample to be analyzed flowed through said through passage, structure defining a sample inlet port, structure connecting said sample inlet port to said inlets of said first and second analysis regions, control structure in said housing structure for flowing a sample to be analyzed from said sample inlet port through said first and second analysis regions, and output structure coupled to said first and second analysis regions for providing output data as a function of the outputs of said FTIR system and said polychromator system as a function of the liquid sample flowed through said first and second analysis regions.

2. The system of claim 1 wherein said FTIR analysis system includes a flow through cell comprising a pair of spaced plate members, said first analysis region being disposed between said plate members, interferometer structure for generating a beam of radiation for passage through said plate members and said first analysis region, and sensor structure for sensing the beam of radiation passed through said plate members and said first analysis region for generating FTIR analysis information as function of the liquid sample disposed in said first analysis region.

3. The system of claim 1 wherein said polychromator system includes entrance slit structure, exit slit structure composed of a plurality of exit slit regions, and radiation dispersing structure for dispersing radiation passing through said entrance slit structure into a spectrum for application to said exit slit regions.

4. The system of claim 1 wherein each said metal electrode contains at least ninety-nine percent of a particular metal.

5. The system of claim 4 wherein said particular metal of each said electrode is silver.

6. The system of claim 1 wherein said second analysis region includes sample excitation apparatus disposed in an enclosed chamber, said chamber having an outlet port across which filter structure is disposed, and structure for flowing gas from said chamber through said filter structure for exhaust outside said housing structure.

7. The system of claim 1 wherein said second analysis region includes sample excitation apparatus disposed in an enclosed chamber, and said sample excitation apparatus includes a pair of spaced main electrodes and a pair of trigger electrodes disposed in spaced relation to said main electrodes in said analysis region such that the breakdown of the gap between said trigger electrodes generates ultraviolet radiation to preionize the gap between said main electrodes.

8. The system of claim 1 and further including wheel structure on which said housing structure is mounted so that said analysis system is relatively mobile.

9. The system of claim 1 wherein said housing structure includes shock absorbing structure, and said polychromator system is mounted on said shock absorbing structure.

10. An analytical system for analyzing a liquid sample comprising housing structure, structure in said housing structure defining a first analysis region having an inlet and an outlet, a FTIR analysis system disposed in sensing relation to said first analysis region, structure in said housing structure defining a second analysis region having an inlet and an outlet, a polychromator system disposed in sensing relation to said second analysis region, structure defining a sample inlet port, structure connecting said sample inlet port to said inlets of said first and second analysis regions, control structure in said housing structure for flowing a sample to be analyzed from said sample inlet port through said first and second analysis regions, said control structure including a pump that has forward and reverse modes of operation, said first and second analysis regions being connected in series, and said control structure flowing a sample to be analyzed at a first flow rate into said first analysis region with said pump being stopped during an FTIR analysis cycle, and said pump being operated in a reverse flow mode during a first part of a polychromator analysis cycle to remove excess sample material from the second analysis region and then in a relatively low forward flow rate mode during a second part of said polychromator analysis cycle, and output structure coupled to said first and second analysis regions for providing output data as a function of the outputs of said FTIR system and said polychromator system as a function of the liquid sample flowed through said first and second analysis regions.

11. The system of claim 10 wherein said relatively low forward flow rate is less than one-half said first flow rate.

12. A process for analyzing liquid sample material such as a lubricating oil comprising the steps of:

providing a first analysis region with an FTIR analysis system disposed in sensing relation to said first analysis region, providing structure defining a second analysis region with a polychromator system disposed in sensing relation to said second analysis region, flowing a liquid sample to be analyzed into said first analysis region, stopping the liquid sample flow while said liquid sample is in said first analysis region and subjecting that liquid sample in said first analysis region to an FTIR analysis sequence, flowing the liquid sample into said second analysis region, reversing the flow direction to remove excess sample from said second analysis region, resuming flow in the forward direction at a low flow rate and concurrently subjecting said liquid sample in said second analysis region to an electric discharge to excite the liquid sample to spectroemissive levels for sensing by said polychromator system.

13. The process of claim 12 wherein said liquid sample is a lubricating oil material, said polychromator system senses for metal constituents in said lubricating oil, and said FTIR system senses for constituents such as glycol, water, fuel and soot.

14. An analytical system for analyzing a liquid sample comprising:

structure defining an analysis region having an inlet and an outlet, a spectrometer system disposed in sensing relation to said analysis region, structure defining a sample inlet port, structure connecting said sample inlet port to said inlet of said analysis region, said analysis region including sample excitation apparatus with a pair of spaced metal electrodes, one of said electrodes having an upper surface in spaced juxtaposition to the other electrode and passage structure connected to said inlet of said analysis region, said one metal electrode being disposed with said passage structure extending to an outlet port in said upper surface, and structure in said upper surface defining a plurality of channels extending away from said outlet port of said passage structure for discharge of excess quantities of a liquid sample to be analyzed flowed through said passage structure, control structure for flowing a sample to be analyzed from said sample inlet port through said analysis region, and output structure coupled to said analysis region for providing output data as a function of the output of said spectrometer system as a function of the liquid sample flowed through said analysis region.

15. The system of claim 14 wherein said control structure for flowing a sample includes a pump that has forward and reverse modes of operation, and said control structure operates said pump in a reverse flow mode during a first part of a spectrometer analysis cycle to remove excess sample material from said analysis region and then in a relatively low forward flow rate mode during a second part of said spectrometer analysis cycle.

16. The system of claim 14 wherein said sample excitation apparatus is disposed in an enclosed chamber, said chamber having an outlet port across which filter structure is disposed, and structure for flowing gas from said chamber through said filter structure for exhaust outside said housing structure.

17. The system of claim 16 and further including wheel structure on which said housing is mounted so that said analysis system is relatively mobile.

18. The system of claim 14 wherein said spectrometer system includes entrance slit structure, exit slit structure composed of a plurality of exit slit regions, and radiation dispersing structure for dispersing radiation passing through said entrance slit structure into a spectrum for application to said exit slit regions.

19. The system of claim 18 wherein said sample excitation apparatus is disposed in an enclosed chamber, said chamber having an outlet port across which filter structure is disposed, and structure for flowing gas from said chamber through said filter structure for exhaust outside said housing structure.

20. The system of claim 19 and further including wheel structure on which said housing structure is mounted so that said analysis system is relatively mobile.

21. The system of claim 20 wherein said housing structure includes shock absorbing structure, said spectrometer system is mounted on said shock absorbing structure.

22. The system of claim 21 wherein said control structure for flowing a sample includes a pump that has forward and reverse modes of operation, and said control structure operates said pump in a reverse flow mode during a first part of a polychromator analysis cycle to remove excess sample material from said analysis region and then in a relatively low forward flow rate mode during a second part of said polychromator analysis cycle.

23. The system of claim 22 wherein said relatively low forward flow rate is less than one-half said first flow rate.

24. The system of claim 14 wherein each said metal electrode contains at least ninety-nine percent of a specific metal.

25. The system of claim 23 wherein said specific metal is silver.

26. An analytical system comprising:

structure defining an analysis region, a spectrometer system disposed in sensing relation to said analysis region, said analysis region including sample excitation apparatus with a pair of spaced main electrodes, and a pair of trigger electrodes disposed in spaced relation to said main electrodes in said analysis region such that the breakdown of the gap between said trigger electrodes generates ultraviolet radiation to preionize the gap between said main electrodes, one of said main electrodes has an upper surface in spaced juxtaposition to the other main electrode, said one main electrode having passage structure extending to an outlet port in said upper surface, and structure in said upper surface defining a plurality of channels extending away from said outlet port of said passage structure for discharge of excess quantities of a liquid sample to be analyzed flowed through said passage structure, and output structure coupled to said analysis region for providing output data as a function of the output of said spectrometer system as a function of the sample in said analysis region.

27. The system of claim 26 and further including housing structure in which said spectrometer system and said analysis region are disposed; said housing structure including shock absorbing structure, and said spectrometer system being mounted on said shock absorbing structure.

28. A process for analyzing liquid sample material such as a lubricating oil comprising the steps of:

providing structure defining an analysis region with a polychromator system disposed in sensing relation to said analysis region, said polychromator system including entrance slit structure, exit slit structure composed of a plurality of exit slit regions, and radiation dispersing structure for dispersing radiation passing through said entrance slit structure into a spectrum for application to said exit slit regions, flowing a liquid sample to be analyzed into said analysis region at a first flow rate, reversing the flow direction to remove excess liquid sample from said analysis region, resuming flow in the forward direction at a low flow rate and concurrently subjecting said liquid sample in said analysis region to an electric discharge to excite the liquid sample to spectroemissive levels for sensing by said polychromator system.

29. The process of claim 28 wherein said analysis region includes sample excitation apparatus that includes a pair of spaced metal electrodes, one of said electrodes having an upper surface in spaced juxtaposition to the other electrode and passage structure connected to said inlet of said analysis region, said one metal electrode being disposed with said passage structure extending to an outlet port in said upper surface, and structure in said upper surface defining a plurality of channels extending away from said outlet port of said passage structure for discharge of excess quantities of a liquid sample to be analyzed flowed through said passage structure.

30. The process of claim 29 wherein said liquid sample is a lubricating oil material, and said polychromator system senses metal constituents in said lubricating oil material.

31. The process of claim 29 wherein each said metal electrode contains at least ninety-nine percent silver.

32. The process of claim 28 wherein said analysis region includes sample excitation apparatus that includes a pair of spaced electrodes, and a pair of spaced main trigger electrodes, one of said main electrodes has an upper surface in spaced juxtaposition to the other main electrode, said one main electrode having passage structure extending to an outlet port in said upper surface, and structure in said upper surface defining a plurality of channels extending away from said outlet port of said passage structure for discharge of excess quantities of a liquid sample to be analyzed flowed through said passage structure, said trigger electrodes being disposed in adjacent spaced relation to said main electrodes such that the breakdown of the gap between said trigger electrode generates ultraviolet radiation to preionize the gap between said main electrodes, and subjecting said liquid sample in said analysis region to an electric discharge between said main electrodes to excite the liquid sample to spectroemissive levels for sensing by said polychromator system.

33. The process of claim 32 wherein said relatively low forward flow rate is less than one-half said first flow rate.

* * * * *

UNITED STATES PATENT AND TRADEMARK OFFICE
CERTIFICATE OF CORRECTION

PATENT NO. : 5,610,706

DATED : March 11, 1997

INVENTOR(S) : Charles E. Carroll et al.

It is certified that error appears in the above-identified patent and that said Letters Patent is hereby corrected as shown below:

Col. 4, line 44, "gramting" should be --grating--.

Col. 9, claim 25, line 22, "claim 23" should be --claim 24--.

Signed and Sealed this

Twenty-fifth Day of November, 1997

Attest:

BRUCE LEHMAN

Attesting Officer

Commissioner of Patents and Trademarks